United States Patent [19]

Massardo et al.

[11] 4,317,905
[45] Mar. 2, 1982

[54] PREPARATION OF COMPOUNDS CONTAINING TWO CONJUGATED DOUBLE BONDS CIS-CIS AND CIS-TRANS

[75] Inventors: Pietro Massardo, Milan; Giorgio Cassani, Arluno; Paolo Piccardi, Milan, all of Italy

[73] Assignee: Montedison S.p.A., Milan, Italy

[21] Appl. No.: 41,064

[22] Filed: May 21, 1979

Related U.S. Application Data

[63] Continuation-in-part of Ser. No. 941,215, Sep. 11, 1978, abandoned.

[30] Foreign Application Priority Data

Sep. 14, 1977 [IT] Italy ............................... 27519 A/77

[51] Int. Cl.$^3$ ................... C07D 309/12; C07C 67/14; C07C 67/08; C07C 41/48; C07C 5/09; C07C 1/36
[52] U.S. Cl. ............................. 542/413; 260/345.9 R; 560/261; 568/596; 568/597; 568/598; 568/855; 568/857; 568/873; 568/903; 585/254; 585/534; 585/601
[58] Field of Search ................ 560/261; 568/597, 596, 568/598, 903, 908, 873; 260/345.9 R; 585/534, 601, 254; 542/413

[56] References Cited

U.S. PATENT DOCUMENTS 3,931,326  1/1976  Kovats et al. ..................... 560/261
3,985,813 10/1976  Labovitz et al. ................... 560/261
3,996,270 12/1976  Friedman et al. .................. 560/261

Primary Examiner—Vivian Garner
Attorney, Agent, or Firm—Stevens, Davis, Miller & Mosher

[57] ABSTRACT

A process is disclosed for preparing aliphatic compounds containing two conjugated double bonds cis-cis or cis-trans, characterized in that a compound of the general formula

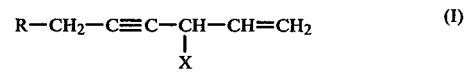

(in which R is H, alkyl from $C_1$ to $C_{10}$, or OY in which Y is a protective group selected from the class consisting of tetrahydropyranyl and 1-ethoxyethyl; X is an ester function selected from the class consisting of the acetates) is reacted with an alkyl-magnesium halide of the general formula:

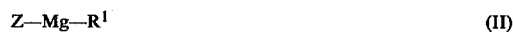

(in which Z is chlorine, bromine or iodine, and $R^1$ is a $C_1$-$C_{10}$ alkyl group, or a group $(CH_2)_n$ OY in which Y has the same meaning as in formula (I), and n is a number from 3 to 10) in the presence of $Li_2CuCl_4$, CuCl, CuBr, or CuI at temperatures ranging from about $-30°$ to $+10°$ C. in the presence of ethyl ether or tetrahydrofuran as solvent, to obtain an aliphatic compound of the general formula:

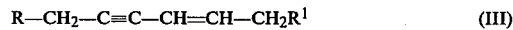

in which the carbon atoms linked with the double bond carry two hydrogen atoms in cis position, and reducing the triple bond of (III) with lithium-aluminum hydride to produce the trans-cis compound, or reducing (III) with dialkylborane or catecholborane to produce the cis-cis compound.

4 Claims, No Drawings

PREPARATION OF COMPOUNDS CONTAINING TWO CONJUGATED DOUBLE BONDS CIS-CIS AND CIS-TRANS

This application is a continuation-in-part of our prior copending application Ser. No. 941,215, filed Sept. 11, 1978, and now abandoned.

This invention relates to a process for preparing aliphatic compounds containing two conjugated double bonds cis-cis and cis-trans.

More particularly, it relates to the synthesis mentioned above and to its application to the preparation of cis, trans-9,11-tetradecadienyl-acetate, which is well known as the main component of the sexual attractant (pheromone) of *Spodoptera litoralis* and of *Spodoptera litura*, two lepidopters that infest important cultivated areas, the former in Europe and Africa and the latter in Japan.

The synthesis of cis-trans-9,11-tetradecadienyl-acetate has already been realized by various workers (see British Patent No. 1,435,621, or D. R. Hall et al., *Chem. Industry*, 1975, p. 216; G. Groto et al., *Chem. Letters*, 1975, p. 103). However, these prior processes are difficult to practice industrially because of the complexity of the syntheses described as well as the expensive purification methods involved.

For example, according to the above-cited British patent, one starts from 10-(2-tetrahydropyranyloxy-)dec-1-ynyl magnesium bromide, which is reacted with butyraldehyde to obtain 14-(-2-tetrahydropyranyloxy-)-tetradec-5-yn-4-ol, which is then dehydrated to 2-(-tetradec-11-en-9-ynyloxy-)-tetrahydropyranyl(cis, trans mixture); the latter, after acetylation and reduction, provides a cis-cis and cis-trans mixture of 9,11-tetradecadienyl-acetate. To obtain the desired cis-trans compound, a difficult and expensive separation of the isomers is required.

It is therefore an object of the present invention to provide a simple and stereospecific synthesis of aliphatic compounds containing a double bond conjugated with a triple bond, in which the double bond is exclusively "cis".

Another object is that of preparing, by reduction of the triple bond, conjugated diene compounds having selectively the cis-cis or cis,trans configuration.

A still further object is that of providing a stereospecific synthesis of cis,trans-9,11-tetradecadienyl-acetate. Moreover, the compounds tridec-4-en-2-yn-1,13-diol and tridec-2,4-dien-1,13-diol are provided.

These and still other objects of this invention are achieved by the process consisting or consisting essentially of the following steps:

(1) Reaction between a compound containing a double bond and a triple bond of the general formula:

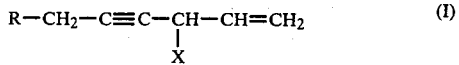

(in which R is H, alkyl from $C_1$ to $C_{10}$, or OY in which Y is a protective group selected from the class consisting of tetrahydropyranyl and 1-ethoxyethyl; X is an ester function selected from the class consisting of the acetates) with an alkyl-magnesium halide of the general formula:

(in which Z is chlorine, bromine or iodine, and $R^1$ is a $C_1$-$C_{10}$ alkyl group, or a group $(CH_2)_nOY$ in which Y has the same meaning as in formula (I), and n is a number from 3 to 10) in the presence of $Li_2CuCl_4$, CuCl, CuBr, or CuI at temperatures ranging from about $-30°$ to $+10°$ C. in the presence of ethyl ether or tetrahydrofuran as solvent.

An aliphatic compound of the general formula:

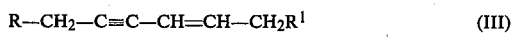

is thus obtained, in which the carbon atoms linked with the double bond carry two hydrogen atoms in cis position.

(2) Reduction of the triple bond of compound (III) either with lithium aluminum hydride to obtain a compound of the general formula:

in which the carbon atoms linked with the double bonds carry two hydrogen atoms in trans-cis position, or with a dialkylborane or catecholborane to obtain the cis-cis isomer.

The new compounds tridec-4-en-2-yn-1,13-diol and tridec-2,4-dien-1,13-diol are thus obtained.

The reaction scheme of the present invention can be employed for the synthesis of the pheromone of *Spodoptera litoralis*. In fact, starting from compound (I) with $R=CH_3$ and using an alkyl-magnesium halide (II) with $R^1$ equal to 7-(2-tetrahydropyranyloxy)-heptyl, the resulting compound (III) is cis-2-(tetradec-9-en-11-ynyloxy)-tetrahydropyran.

The latter compound, by hydrolysis of the tetrahydropyranyl group, reduction with lithium-aluminum hydride, and acetylation provides cis,trans-9,11-tetradecadienyl-acetate, identical with the pheromone of *Spodoptera litoralis* and *litura*, as comparative tests on the biological activity show (see Example 1e).

The case exemplified above is only one of the products readily obtainable by the process of the present invention. Generally, all the compounds of the general formula (III), in which the carbon atoms linked with the double bond carry two hydrogen atoms in cis position, are obtainable. From them, by reduction of the triple bond with stereospecific reducing agents such as lithium-aluminum hydride to obtain a reduction of the triple bond to a trans double bond, or such as dialkyl-boranes to obtain a reduction to a cis double bond, it is possible to prepare (selectively) all the compounds having two conjugated double bonds of the general formula:

$$R-CH_2-CH=CH-CH=CH-CH_2R^1.$$

The following examples are given still better to illustrate the present invention.

EXAMPLE 1

Synthesis of cis,trans-9,11-tetradecadienyl-acetate (I)

(a) Reaction:

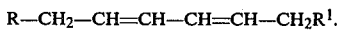

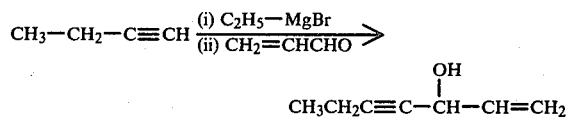

27.25 g of ethyl bromide were added dropwise at room temperature to 250 ml of anhydrous ether containing 7 g of metallic magnesium. The solution was stirred until complete disappearance of the ethyl bromide to obtain CH₃—CH₂—MgBr.

15.3 g of 1-butyne at 35° C. were then bubbled thereinto under intense stirring, carrying out an effective reflux by means of a condenser at −78° C.

The reaction mixture was cooled to 20° C., whereupon 16.25 ml of acrylic aldehyde dissolved in 25 cc of anhydrous ether were added thereto. The whole was gradually brought to room temperature a saturated solution of NH₄Cl in water was added, and the mixture was extracted with water.

The whole, once dehydrated with anhydrous sodium sulphate, and after evaporation of the ether, yielded 20.4 g of

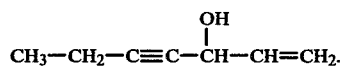
(1)

(b) Reaction:

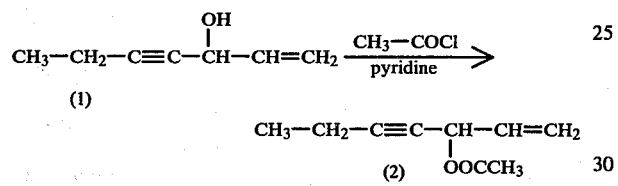

3.5 g of (1) and 2.1 ml of pyridine were dissolved in 60 cc of ether. At room temperature, 2.2 ml of CH₃COCl in 3 cc of ethyl ether were dropped thereinto. After 2 hours 50 ml of water and ice were added, and the separated ether solution was dehydrated and concentrated.

The unrefined product was purified by chromatography in a silica gel column, eluting with petroleum ether. 3 g of

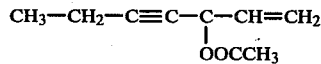

were thus obtained.

(c) Reaction:

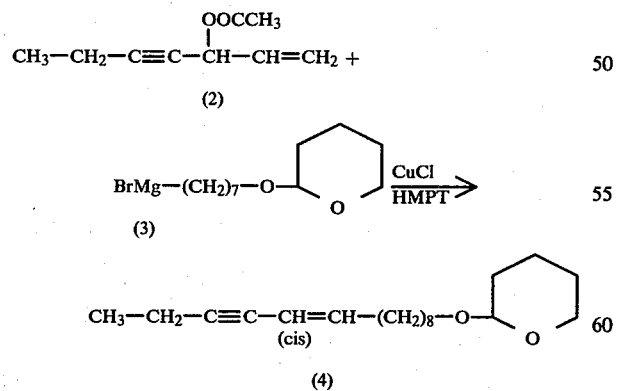

4 g of 2-(7-bromo-1-heptanoxy)-tetrahydropyran dissolved in 8 cc of tetrahydrofuran were dropped into 0.5 g of metallic magnesium in 2 cc of anhydrous tetrahydrofuran (THF) containing crystal iodine, to give (3). The reaction mixture was heated to 60° C. for 1 hour and then cooled down with ice and added dropwise at −10° C. to a solution, in 4 cc of tetrahydrofuran, of 0.043 g of CuCl, 2 g of (2), and 0.16 ml of hexamethyl-phosphoryl-triamide (HMPT).

After 2 hours at −10° C., the whole was brought to room temperature, the reaction mixture was treated with a saturated aqueous solution of NH₄Cl, and repeatedly extracted with ether.

The ether solution, after dehydration, was concentrated under vacuum, thus obtaining 4.7 g of a mixture containing

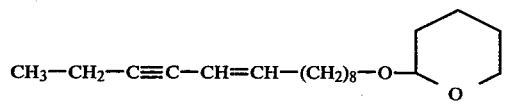

(d) Reaction:

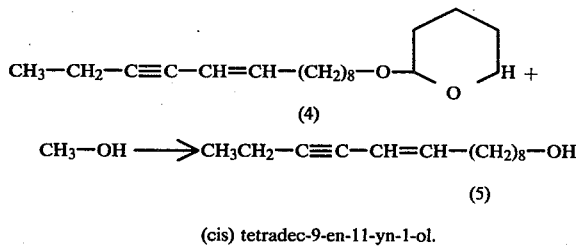

(cis) tetradec-9-en-11-yn-1-ol.

The unrefined reaction product was diluted in 50 cc of methyl alcohol additioned with 2 cc of 10% HCl in water and allowed to stand overnight. Successively the alcohol was evaporated under vacuum, the residue was dissolved into ether washed with salt-saturated water, dehydrated and concentrated.

The product was then purified by chromatography in a silica gel column, eluting with hexane (95 parts) and ethyl ether (5 parts). 2.2 g of pure product (5) were obtained.

(e) Reaction:

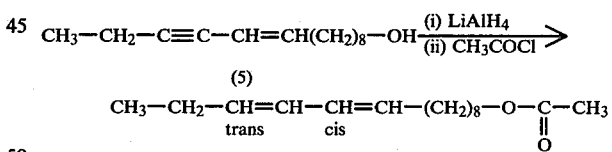

Into a suspension of 0.6 g of LiAlH₄ in 11 cc of diethylene glycol dimethylether and 1.5 cc of THF, heated to 140° C. to remove the low boiling components and then cooled to 10° C., there were added 1.5 g of (5) dissolved in 1.5 cc of diethylene glycol dimethylether. The mixture was heated up to 140° C. and was then kept at such temperature for 2 hours. It was successively cooled and gradually hydrolyzed with iced water. The aqueous layer was neutralized with dilute hydrochloric acid. A floating upper layer of organic substance thus separated, which was extracted with ether and dehydrated with anhydrous sodium sulphate. The ether solution was filtered, treated with 0.4 ml of pyridine, and then with 0.4 ml of acetyl chloride. It was maintained at room temperature for 2 hours, whereupon the reaction solution was washed with water and with NaCl-saturated water, dehydrated over Na₂SO₄, and concentrated under vacuum by means of a mechanical pump to remove the low boiling material.

1.3 g of (cis,trans)-9,11-tetradecadienyl-acetate were obtained (purity=93%, determined by gas-chromatography).

This product was further purified by liquid chromatography at high pressure and identified on the basis of a comparison by gas-chromatography with a product prepared as illustrated by G. Groto (*Chem. Letters*, l.c.) and on the basis of the IR and NMR spectra. Coincident results were obtained as regards both the comparison between the samples and the data specified in the literature.

The attractive activity towards the males of *Spodoptera litoralis* was tested in comparison with a pheromone sample prepared according to the synthesis method of G. Groto (l.c.), in respect of which the sample of the present invention was identical as regards all the chemical and physical characteristics. The method chosen was the conventional one of electro-antennography.

Such method enables one to record the impulse generated by the antenna of a male of *Spodoptera litoralis* when, after having been inserted into a proper amplifying circuit, it is contacted with an air flow containing traces of pheromone.

The two substances gave equal positive responses, thus confirming also the identity of their biological activity.

EXAMPLE 2

Synthesis of non-5-en-3-yne

Reaction:

$$CH_3-CH_2-C\equiv C-\underset{\underset{OOCCH_3}{|}}{CH}-CH=CH_2 +$$

(2)

$$CH_3-CH_2MgBr \longrightarrow$$
$$CH_3-CH_2-C\equiv C-CH=CH-CH_2-CH_2-CH_3$$

Under nitrogen, and in a completely anhydrous environment at $-10°$ C., 12 ml of $CH_3CH_2MgBr$, 0.1 mole of tetrahydrofuran were dropped into a solution of 1.2 g of compound (2), 0.025 g of CuCl, and 0.91 g of triethyl phosphite in 6 ml of THF.

The reaction mixture was kept at $-10°$ C. for 1 hour and then brought to room temperature.

It was neutralized with an ammonium chloride-saturated solution, repeatedly extracted with hexane, and dehydrated.

After evaporation of the low boiling materials, there were obtained 0.85 g of unrefined product containing the isomerically pure addition product (90%) non-5-en-3-yne having the following characteristics:

mass spectrophotometry m/e 122
IR-spectrum λ max $(-C\equiv C-)$ 2220 and $$(-\overset{H}{\underset{|}{C}}=\overset{H}{\underset{|}{C}}-)$$

740 cm$^{-1}$.

EXAMPLE 3

Preparation of cis-dodec-7-en-9-ynylacetate
Reaction:

$$CH_3-CH_2-C\equiv C-\underset{\underset{OOCCH_3}{|}}{CH}-CH=CH_2 +$$

(2)

$$BrMg-(CH_2)_5-OThP \longrightarrow$$

$$CH_3-CH_2-C\equiv C-CH=CH-(CH_2)_6-OThP$$
cis

Under nitrogen, and in a completely anhydrous environment at $-10°$ C., 20 ml of a 1 M solution in THF of 5-(2-tetrahydropyranyloxy-pentyl)magnesium bromide [$BrMg-(CH_2)_5-OThP$], were dropped into a solution in 10 ml of THF of 2 g of compound (2), 0.04 g of CuCl, and 0.13 ml of hexamethylphosphoryl triamide. The reaction mixture was kept at $-10°$ C. for 1 hour, then, at room temperature, it was treated with an aqueous $NH_4Cl$-saturated solution. The reaction products were extracted with hexane and, after dehydration, they were concentrated. 4 g of unrefined product were obtained, which were dissolved in 20 ml of acetic acid and 2 ml of acetyl chloride, and heated for 2 hours to 35°–40° C. The reaction mixture was then poured into water and ice and repeatedly extracted with hexane.

From the hexane solution, dehydrated over anhydrous $Na_2SO_4$ and concentrated under vacuum, 3.3 of unrefined product were obtained. This product, further purified by chromatography in a silica gel column (eluent: 98% of hexane, 2% of ethyl ether), yielded 2.3 g of cis-dodec-7-en-9-ynyl acetate:

$$CH_3-CH_2-C\equiv C-CH=CH-(CH_2)_6-O-COCH_3$$

IR-spectrum: $\lambda_{max}$ $(-C\equiv C-)$ 2220, (C=O) 1740

$$G(-\overset{H}{\underset{|}{C}}=\overset{H}{\underset{|}{C}})$$

740

Spectrum of H$^1$ NMR: (CDCl$_3$)=1.2 (3H,t,$-CH_3$), 1.2–1.9 (8H, complex, $-(CH_2)_4-$), 2.05 (3H,s,CH$_3-CO-$), 2.05–2.6 (4H complex), 4.1 (2H,t,$-CH_2-O$), 5.45 and 5.85 (2H, multiplet, $-CH_A=CH_B-$, $J_{AB}-11$ Hz).

EXAMPLE 4

Reduction of cis-dodec-7-en-9-ynyl-1 acetate to cis,cis-7,9-dodecadienyl-acetate Reaction:

A mixture consisting of 1.330 g (0.6·10$^{-2}$ moles) of cis-dodec-7-en-9-ynyl-acetate and of 0.72 g (0.6·10$^{-2}$ moles) of catecholborane in 12 cc of THF was stirred for 3 days at 29° C. in a nitrogen atmosphere.

1 cc of CH$_3-$COOH were added thereto and the whole was heated at reflux temperature under reflux conditions for 2 hours, always in a nitrogen atmosphere.

The cooled solution was poured into water and ice and extracted with pentane. The organic phase in pentane was washed with a 1 N solution of NaOH, then with an NaCl-saturated solution, and finally dried on magnesium sulphate.

By evaporation of the solvent and by separation of the unreacted alkyne by liquid chromatography at high pressure, 0.950 g of cis,-cis-7,9-dodecadienyl-acetate was obtained.

Spectrum of $^1$H NMR (CDCl$_3$)$\delta$=1.0 (3H,t,—CH$_3$), 1.2–1.7 (8H, complex, —(CH$_2$)$_4$—), 2.05 (3H,s,CH$_3$—CO) 1.9–2.5 (4H, complex), 4.05 (2H,t,—CH$_2$—O), 5.2–6.3 (4H, multiplet, —CH=CH—CH=CH—).

EXAMPLE 5

Synthesis of (cis)hept-4-en-2-yn-1-ol

The reaction:

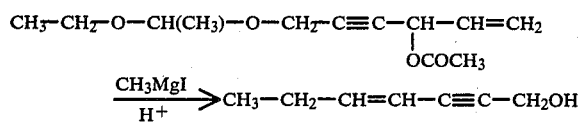

Into an ethereal (150 ml) solution of 11 g of 3-acetoxy-7,9-dioxa-8-methyl-undec-1-en-4-yn containing 0.06 g CuCl and 0.22 g of hexamethylphosphoramide kept under nitrogen, 50 ml of a 1.4 molar solution of CH$_3$MgI in ether were dripped. After 1 hour, an aqueous saturated solution of NH$_4$Cl was added and the ethereal layer was separated and concentrated.

The residue was taken up in methanol containing 0.5% of HCl in order to remove the protective group. The mixture was stirred two hours, neutralized, dissolved in anhydrous ether, concentrated, and distilled under vacuum. 3.2 of (cis) hept-4-en-2-yn-1-ol, b.p. 90° at 7 mm Hg, were obtained.

EXAMPLE 6

Synthesis of (cis) tridec-4-en-2-yn-1,13-diol

The reaction:

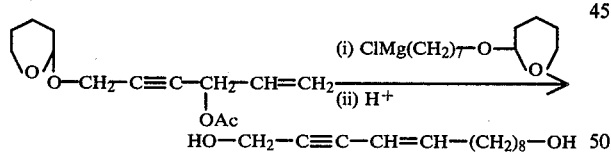

Into a solution of 16.7 g of 4-acetoxy-hex-5-en-2-ynyl-tetrahydropyranyl-ether in 100 ml of tetrahydrofuran kept under nitrogen and containing 10 ml of a 0.1 molar solution of Li$_2$CuCl$_4$ in tetrahydrofuran, 100 ml of a molar solution of 7-tetrahydropyranyloxy-heptyl-magnesium chloride in tetrahydrofuran were dripped at −20° C. The temperature was allowed to rise slowly to 0° C. and, after two hours at this temperature, an aqueous solution of 10% HCl was added up to a faint acidity.

The mixture was stirred overnight, and then neutralized and extracted with ethyl ether. After separation of the layers and concentration of the organic solvent under vacuum, 15 g of a mixture containing cis-tridec-4-en-2-yn-1,13 diol which was used as such in the subsequent example was obtained.

The pure product was obtained by thin layer chromatography. It showed H rm.n, $\delta$(CD Cl$_3$):1.2–1.7 (12 H complex); 2.3 (2Hm); 3.1(2H,s); 3.6 (2HT); 4.4 (2H,s); 5.2–6.2 (2Hm).

EXAMPLE 7

Synthesis of tridec-2,4-dien-1,13-diol

The reaction:

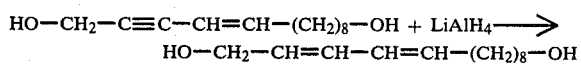

In a nitrogen atmosphere and under vigorous stirring, 13 g of the mixture of the preceding example containing cis-tridec-4-en-2-yn-1,13-diol dissolved in 120 ml of 1,2-dimethoxyethane were dripped at 20° C. into a suspension of LiAlH$_4$ (2.4 g) in 100 ml of 1,2-dimethoxyethane. The whole was heated at 30° C. for 2 hours, then cooled down and poured carefully onto ice.

After neutralization with 10% aqueous H$_2$SO$_4$, it was extracted with ethyl-ether. The ethereal layer was dried and concentrated under vacuum.

The residue was purified by crystallization from a mixture of ethyl ether-petroleum ether.

The crystallizate, having a m.p. of 42° C., weighed 10 g. 1 H.r. m.n., $\delta$(CDCl$_3$)=1.2–1.7 (12H complex); 1.9–2.2 (4H complex); 3.6 (2H,t); 4.1 (2H, d); 5.0–6.8 (4H, m).

What is claimed is:

1. A process for preparing aliphatic compounds containing two conjugated double bonds cis-cis or cis-trans, characterized in that a compound of the general formula:

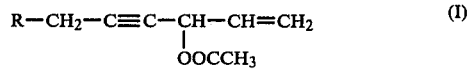

(in which R is H, alkyl from C$_1$ to C$_{10}$, or OY in which Y is a protective group selected from the class consisting of tetrahydropyranyl and 1-ethoxyethyl is reacted with an alkyl-magnesium halide of the general formula:

(in which Z is chlorine, bromine or iodine, and R$^1$ is a C$_1$–C$_{10}$ alkyl group, or a group (CH$_2$)$_n$OY in which Y has the same meaning as in formula (I), and n is a number from 3 to 10) in the presence of Li$_2$CuCl$_4$, CuCl, CuBr, or CuI, and optionally in the presence of triethyl phosphite or hexamethylphosphoryl triamide, at temperatures ranging from about −30° to +10° C. in the presence of ethyl ether or tetrahydrofuran as solvent, to obtain an aliphatic compound of the general formula:

in which the carbon atoms linked with the double bond carry two hydrogen atoms in cis position, and reducing the triple bond of (III) with lithium-aluminum hydride to produce the cis-trans compound, or reducing (III) with dialkylborane or catecholborane to produce the cis-cis compound.

2. The process as claimed in claim 1, in which the reaction between compound (I) and compound (II) is conducted in the presence of triethylphosphite or hexamethylphosphoryl triamide.

3. A process for preparing aliphatic compounds having the general formula (III) as set forth below, characterized in that a compound of the general formula:

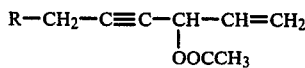 (I)

(in which R is H, alkyl from $C_1$ to $C_{10}$, or OY in which Y is a protective group selected from the class consisting of tetrahydropyranyl and 1-ethoxyethyl is reacted with an alkylmagnesium halide of the general formula:

 (II)

(in which Z is chlorine, bromine or iodine, and $R^1$ is a $C_1$-$C_{10}$ alkyl group, or a group $(CH_2)_nOY$ in which Y has the same meaning as in formula (I), and n is a number from 3 to 10) in the presence of $Li_2CuCl_4$, CuCl, CuBr, or CuI at temperatures ranging from about $-30°$ to $+10°$ C. in the presence of ethyl ether or tetrahydrofuran as solvent, to obtain an aliphatic compound of the general formula:

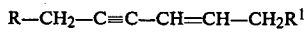 (III)

in which the carbon atoms linked with the double bond carry two hydrogen atoms in cis position.

4. A process for preparing an aliphatic compound containing two conjugated double bonds, characterized in that a compound of the formula:

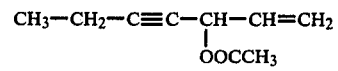 (I)

is reacted with an alkyl-magnesium halide of the general formula:

 (II)

(in which Z is chlorine, bromine or iodine, and $R^1$ is 7-(2-tetrahydropyranyloxy)heptyl) in the presence of $Li_2CuCl_4$, CuCl, CuBr, or CuI, and optionally in the presence of triethyl phosphite or hexamethylphosphoryl triamide, at temperatures ranging from about $-30°$ to $+10°$ C. in the presence of ethyl ether or tetrahydrofuran as solvent, to obtain an aliphatic compound of the general formula:

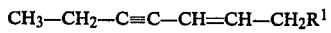 (III)

in which the carbon atoms linked with the double bond carry two hydrogen atoms in cis position, the resulting compound (III) being

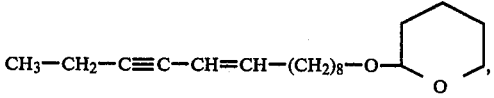

which is thereafter hydrolyzed to give cis-tetradec-9-en-11-yn-1-ol, which is subsequently hydrogenated in the triple bond with lithium-aluminum hydride and acetylated, to produce cis, trans-9,11-tetradecadienylacetate.

* * * * *